United States Patent [19]
Watson et al.

[11] Patent Number: 5,800,376
[45] Date of Patent: *Sep. 1, 1998

[54] BURR-HOLE FLOW CONTROL DEVICE

[75] Inventors: David A. Watson, Goleta; Paul S. Vaskelis, Santa Barbara, both of Calif.

[73] Assignee: Medtronic, Inc., Minneapolis, Minn.

[ * ] Notice: The term of this patent shall not extend beyond the expiration date of Pat. No. 5,662,600.

[21] Appl. No.: 826,782

[22] Filed: Apr. 7, 1997

Related U.S. Application Data

[63] Continuation of Ser. No. 536,651, Sep. 29, 1995.
[51] Int. Cl.$^6$ ........................................ A61F 5/00
[52] U.S. Cl. .................................... 604/9; 604/8
[58] Field of Search ........................ 604/8, 9, 10

[56] References Cited

U.S. PATENT DOCUMENTS

| | | |
|---|---|---|
| 2,867,213 | 1/1959 | Thomas, Jr. . |
| 2,933,102 | 4/1960 | Hillman et al. . |
| 3,021,842 | 2/1962 | Flood . |
| 3,111,125 | 11/1963 | Schulte . |
| 3,288,142 | 11/1966 | Hakim . |
| 3,492,996 | 2/1970 | Fountain . |
| 3,503,402 | 3/1970 | Schulte . |
| 3,527,226 | 9/1970 | Hakim . |
| 3,595,240 | 7/1971 | Mishler .................... 604/9 |
| 3,601,128 | 8/1971 | Hakim . |
| 3,756,243 | 9/1973 | Schulte . |
| 3,758,073 | 9/1973 | Schulte . |
| 3,768,508 | 10/1973 | Schulte . |
| 3,769,982 | 11/1973 | Schulte . |
| 3,827,439 | 8/1974 | Schulte et al. . |
| 3,851,588 | 12/1974 | Taylor . |
| 3,980,097 | 9/1976 | Ellis . |
| 4,084,606 | 4/1978 | Mittleman . |
| 4,364,395 | 12/1982 | Redmond et al. . |
| 4,475,899 | 10/1984 | Muller . |
| 4,560,375 | 12/1985 | Schulte et al. . |
| 4,636,194 | 1/1987 | Schulte et al. .................... 604/9 |
| 5,176,627 | 1/1993 | Watson .......................... 604/9 |
| 5,662,600 | 9/1997 | Watson et al. ................. 604/9 |

OTHER PUBLICATIONS

PS Medical CSF–Flow Control Shunts by Pudenz Schulte Medical, 28 pages.
Brochure for a Radionics Burr Hole Valve (2 pages).
Bruchure from Codman & Shurtleff, Inc. for an Accu–Flo Pressure Valve dated Oct., 1985.
Brochure from Heyer–Schulte Mishler for a Dual Chamber Flushing Valve, Burr Hole Design, dated Mar., 1985.
p. 1–11 and 48–52 from a Bruchure from PS Medical for Delta Burr Hole Valves, dated Apr., 1994.
Codman Accu–Flo Valve System Hydrocephalus Shunt Systems, by Codman & Shurtleff, Inc., 1981, 11 pages.
The Holter–Hausner Products for Neurosurgery, by Holter–Hausner International, 27 pages.
Silastic Hydrocephalus Shunt (Ames Design), by Medical Products Division Dow Corning Corporation, Dec. 1972, 18 pages.

*Primary Examiner*—David Isabella
*Attorney, Agent, or Firm*—Kelly Bauersfeld Lowry & Kelley, LLP

[57] ABSTRACT

A surgically implantable flow control device positionable over a burr-hole through a patient's skull is provided for use in shunt systems for controlling the release of entrapped body fluids. The device includes a rigid base including an inlet port and a valve seat which surrounds the inlet port, and a flow control member secured to the base. The flow control member has an asymmetric membrane which is resiliently biased to contact the valve seat in a manner forming a releasible seal therebetween, to provide controlled resistance to proximal-to-distal fluid flow through the device. The membrane includes a septum portion overlying the inlet port and a relatively thin portion responsive to fluid pressure differentials on inlet and outlet sides thereof. A membrane shield overlies an outlet side of the membrane and includes a needle guide aperture in alignment with the septum portion of the membrane and the inlet port.

23 Claims, 1 Drawing Sheet

BURR-HOLE FLOW CONTROL DEVICE

This is a continuation, of application Ser. No. 08/536,651, filed Sep. 29, 1995.

BACKGROUND OF THE INVENTION

This invention relates generally to surgically implantable valves. More particularly, the present invention relates to one-way flow control valves for controlling the flow of cerebrospinal fluid out of a brain ventricle and preventing backflow of fluid into the brain ventricle.

As is well known in the medical arts, to relieve an undesirable accumulation of fluids it is frequently necessary to provide a means for draining a fluid from one part of the human body to another in a controlled manner. This is required, for example, in the treatment of hydrocephalus, an ailment usually afflicting infants or children in which fluids which ought to drain away accumulate within the skull and thereby exert extreme pressure and skull deforming forces.

In treating hydrocephalus, cerebrospinal fluid accumulated in the brain ventricles is drained away by a catheter inserted into the ventricle through the skull, and the catheter is connected to a tube which conducts the fluid away from the brain to be reintroduced into the vascular system, as by extending through the patient's jugular vein to the atrium portion of the heart, or the peritoneal system. To control the flow of cerebrospinal fluid and maintain the proper pressure in the brain ventricle, a pump or valve is placed in the conduit between the brain and the heart atrium or the peritoneum.

Many such devices have been used in the past, but some prior devices have tended to become obstructed by particulate matter entering the drainage system or by backward diffusion of blood into the system. Further, some prior devices have included moving parts which tended to adhere to other parts of the device and become immobile. When this occurs, the device itself becomes a barrier in the drainage system and it adds to the problem it is intended to solve.

U.S. Pat. Nos. 4,560,375 and 4,636,194 illustrate cerebrospinal fluid flow control valves which overcame many of the drawbacks of the prior art and which have realized great success in the marketplace. However, particularly with prior burr-hole valves, a problem was encountered when surgeons would insert needles into a fluid reservoir to either sample fluid therein or to inject a medication distally. If the needle happened to puncture the fragile flow control membrane, it would be left with an aperture thus destroying the utility of the valve. To counter this, manufacturers have been providing needle guards over the flow control member.

Although such flow control devices are intended to limit the flow of fluid in one direction only, i.e., from a proximal inlet port in fluid communication with the brain ventricle to a distal outlet port in fluid communication with the discharge catheter, it is desirable at times to provide proximal access through the flow control device to the brain ventricle. Prior valve designs which accommodate such proximal access have been less than optimal because they either expose the flow control membrane to unwanted damage by a needle, or more complicated valve designs are required which move the flow control membrane from adjacent the inlet and substitute a septum/flapper component in order to maintain the distal flushing capability of the flow control device.

Accordingly, there has been a long existing need in the medical arts for a convenient and effective device for controlling the flow of fluid from one part of the human body to another, which device is relatively inexpensive to manufacture and which can be constructed of substantially non-metallic parts which are not subject to adhering to one another and causing a malfunction of the device. Additionally, such a device is needed which provides repeated proximal access therethrough without changing the flow control characteristics of the device. As will become apparent from the following description, the present invention satisfies these needs and provides other related advantages.

SUMMARY OF THE INVENTION

The present invention resides in a device useful in shunt systems for controlling the flow of fluids from one part of a body to another. More particularly, the present invention comprises a surgically implantable flow control device having a base including an inlet port and a valve seat surrounding the inlet port, and a flow control member secured to the base. The flow control member includes an asymmetric membrane which is normally biased to prevent flow through the valve, but will open to permit fluid flow therethrough when proximal pressure upstream of the device exceeds distal pressure downstream of the device by a predetermined amount. Further, a membrane shield is provided which overlies an outlet side of the membrane. The membrane shield includes a needle guide aperture in alignment with the inlet port. The flow control device of the present invention is constructed substantially of non-metallic materials which prevent adhesion of one part to another, thereby providing trouble-free and reliable operation of the device. Moreover, the apparatus of the present invention is relatively inexpensive to manufacture and can be easily modified to provide a variety of pressure/flow characteristics.

In a preferred form of the invention, the surgically implantable flow control device comprises a burr-hole flow control valve positionable upon a burr-hole through a patient's skull for controlling proximal-to-distal fluid flow of cerebrospinal fluid from the brain ventricles to another portion of the body. The base is of unitized construction and includes integral inlet and outlet connectors. An inlet passageway is provided through the inlet connector and terminates at the inlet port which is surrounded by the valve seat. A resilient dome overlies a portion of the base to form a reservoir chamber. The outlet includes an outlet port in communication with the reservoir chamber which permits fluid flow through the outlet connector to exit the valve.

The asymmetric membrane is resiliently biased to contact the valve seat in a manner forming a releasable seal therebetween to provide controlled resistance to proximal-to-distal fluid flow through the device. The membrane includes a septum portion overlying the inlet port and a relatively thin portion responsive to fluid pressure differentials on inlet and outlet sides thereof. A membrane shield overlies an outlet side of the membrane and includes a needle guide aperture therethrough in alignment with the septum portion of the membrane and the inlet port. The membrane shield includes prongs which engage the base to hold the membrane shield in place. An alignment plug is fixed to the septum portion of the membrane and extends through the needle guide aperture. The alignment plug may comprise an elastomeric adhesive or it may be molded integrally with the membrane itself.

A variety of pressure/flow characteristics can be provided by the flow control device of the present invention by providing membranes having the relatively thin portions responsive to fluid pressure differentials on the inlet and outlet sides thereof, of varying thickness. The resistance to flow through the device increases with an increase in membrane thickness.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENT

Figure 1:
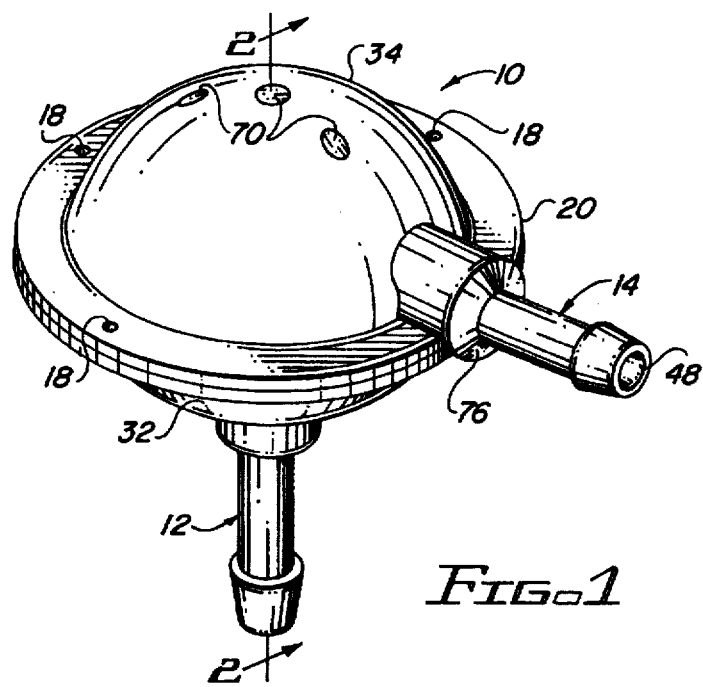
FIG. 1 is a perspective view of a burr-hole flow control device embodying the present invention.

As shown in the drawings for purposes of illustration, the present invention is concerned with a burr-hole flow control device, generally designated in the accompanying drawings by the reference number 10. The improved flow control device 10 is configured to be positionable upon a burr-hole formed through a patient's skull and is intended for use in a surgically implanted shunt system for controlling the proximal-to-distal drainage of cerebrospinal fluid from the brain ventricles to another portion of the body. In order to connect the valve 10 in such a shunt system, the valve includes an inlet connector 12 which normally receives a proximal catheter (not shown), and an outlet connector 14 which receives one end of a piece of surgical tubing (not shown). The tube and catheter each slide over their respective connectors 12 or 14, and each is secured in place by a single ligature preferably tied just inside of an annular ridge 16 formed near the end of each connector.

When the flow control device 10 is used in a drainage shunt system intended for treatment of hydrocephalus, the proximal catheter extends from the connector 12 to a brain ventricle containing cerebrospinal fluid under pressure, and the tube connected to the outlet connector 14 is a distal catheter which serves to discharge cerebrospinal fluid into, for example, the atrium portion of a patient's heart or the peritoneal cavity. Ordinarily, the device 10 will be surgically implanted on the patient's skull immediately over the burr hole, with a flap of skin overlying the valve. To facilitate holding the device 10 in its desired position after implantation, one or more suture holes 18 can be provided on a flange 20 surrounding a portion of the device.

Figure 2:
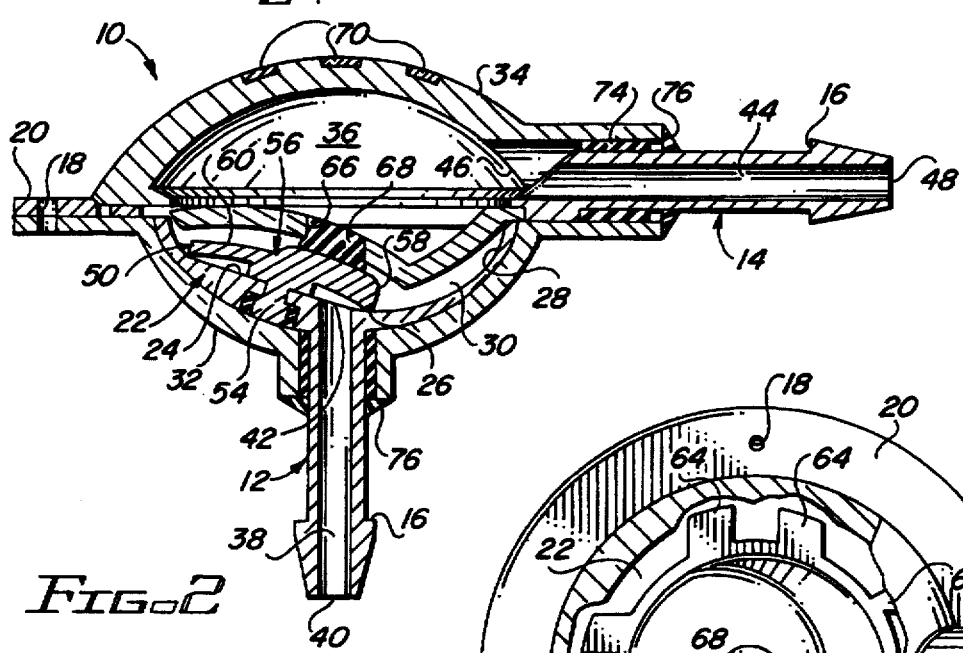
FIG. 2 is an elevational section taken generally along the line 2—2 of FIG. 1.
Figure 3:
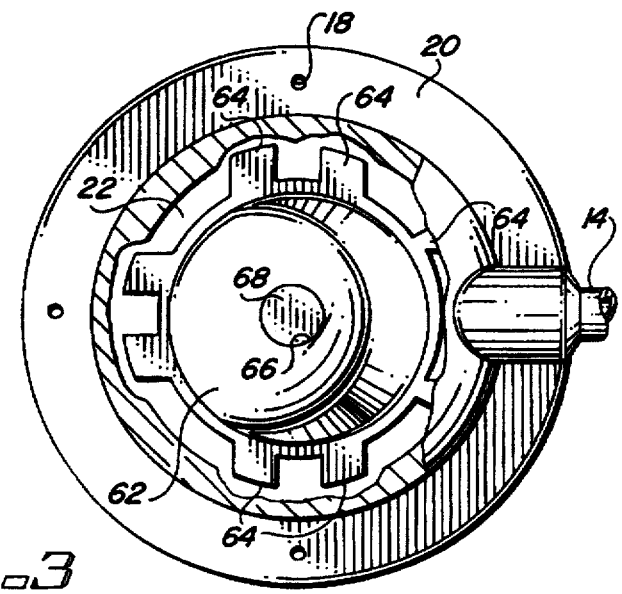
FIG. 3 is a partially sectional plan view wherein the upper dome is cut-away to illustrate the positioning of a membrane shield within the base of the flow control device.

In accordance with the present invention, and as illustrated in FIGS. 1–3, the device 10 is constructed to include a relatively rigid, unitized molded plastic base 22. The base 22 includes a valve supporting portion 24 which forms a valve seat 26, surrounded by a semi-hemispherical portion 28 of the base which defines a well 30. The valve supporting portion 24 is integrally formed with the inlet and outlet connectors 12 and 14.

The base 22 is invested in a lower housing 32 through which the inlet connector 12 protrudes downwardly for placement through the burr-hole. This lower housing 32 sealingly engages about its periphery a resiliently flexible dome 34 to form a reservoir chamber 36 between the dome and the semi-hemispherical portion 28 of the base 22.

An inlet passageway 38 through the device 10 originates at an open end 40 of the inlet connector 12, and terminates at an inlet port 42 situated on the valve supporting portion 24 of the base 22. The inlet port 42 is surrounded by the valve seat 26. An outlet passageway 44 is also provided through the device 10 which originates at an outlet port 46 in fluid communication with the reservoir chamber 36, and terminates at an open end 48 of the outlet connector 14. Fluid traveling through the shunt system utilizing the burr-hole flow control device 10 of the present invention must thus first travel through the inlet passageway 38 to the reservoir chamber 36, and from there through the outlet passageway 44 before being allowed to move to another portion of the body.

The flow control device 10 is arranged for controlling the flow of cerebrospinal fluid out of a brain ventricle and preventing backflow of fluid into the brain ventricle by the provision of a resilient non-metallic flow control member 50. The flow control member 50 is molded of a synthetic polymer material different from the material of the relatively rigid plastic base 22, and includes a central support 52 which is received in a mounting aperture in the base 22 and fixed thereto by an interference fit and use of an adhesive 54, or any other suitable means. The flow control member also includes a resilient membrane 56 integrally molded with the central support 52, which is generally arch-shaped, as for example a section of a sphere, and contacts the valve supporting portion 24 of the base 22 at the valve seat 26 generally along the outer edges of the membrane 56 in a manner surrounding the inlet port 42. The resilient membrane 56 is normally biased to prevent communication between the inlet passageway 38 to the reservoir chamber 36, but will open to permit fluid flow when the pressure in the inlet passageway 38 exceeds the pressure in the reservoir chamber 36 by a predetermined amount. Moreover, should the pressure in the reservoir chamber 36 ever exceed the pressure in the inlet passageway 38, tending to cause fluid flow in a reverse direction (distal-to-proximal) through the valve 10, the membrane 56 will seal tightly against the valve seat 26 and prevent any such reverse flow.

The membrane includes a septum portion 58 which overlies the inlet port 42, and a relatively thin portion 60 which is responsive to fluid pressure differentials on inlet and outlet sides thereof. The septum portion 58 of the resilient membrane 56 is preferably pie-shaped (in a plan view), occupying one fourth to one third of the entire area of the resilient membrane 56. Such an asymmetric membrane 56 utilizes the characteristics of a standard membrane as shown in Pat. No. 4,636,194, but includes a septum to create a thicker, puncturable zone which can be positioned over the inlet port 42 to provide proximal access through the flow control device 10. It is preferable that the septum portion 58 be significantly larger than the inlet port 42 so as to accommodate the insertion of needles therethrough at various needle angles and to minimize the possibility of damage to the thin portion 60 of the membrane 56.

To further protect the thin portion 60 of the resilient membrane 56 and to ensure that any needle inserted through the flow control device 10 to gain proximal access to fluids upstream of the flow control member 50 is allowed to pass through only the septum portion 58, a membrane shield 62 is provided to overlie an outlet side of the membrane 56. The membrane shield is preferably molded of a rigid polypropylene material and includes prongs 64 which engage the base 22 to hold the membrane shield in place. The membrane shield 62 includes a needle guide aperture 66 therethrough in alignment with both the septum portion 58 of the resilient membrane 56 and the inlet port 42. An alignment plug 68 of an elastomeric adhesive is fixed to the septum portion 58 of the membrane 56, and extends through the needle guide aperture 66 to ensure consistent proper positioning of the needle guide aperture directly over the septum portion 58 and the inlet port 42.

The resilient dome 34 is preferably molded of a silicone elastomer material and is designed to permit injection into the reservoir chamber 36 or withdrawal of fluid samples by a hypodermic needle through the dome. The dome 34 is sufficiently resilient to be deformed downwardly by external finger pressure. In this way, the flow control device 10 can be flushed manually in the distal direction by simply manually depressing the dome 34. Sometimes it is desirable to gain access to fluid proximal of the flow control member 50. The provision of a septum portion 58 in the asymmetric membrane 56 makes this possible since the septum portion 58 is capable of resealing upon itself and preventing any fluid flow therethrough upon withdrawal of a needle, in a known manner. The provision of the membrane shield 62 ensures that a needle inserted through the dome 34 will not inadvertently puncture and therefore damage the thin portion 60 of the membrane 56, and the needle guide aperture 66 ensures that any such needle inserted beyond the reservoir chamber 36 is only allowed to pass through the septum portion 58 of the membrane 56.

Since the device 10 of the present invention is primarily designed to provide controlled resistance to cerebrospinal fluid flow from a brain ventricle, it will be appreciated that a physician must be able to select a valve having the particular pressure/flow characteristics desired for each individual application. That is, a valve or flow control member which permits flow at a relatively low pressure differential may not be suitable where the maintenance of a higher pressure differential is indicated. To this end, in order to provide a variety of pressure/flow characteristics, the device 10 can be provided with resilient membranes 56 having the thin portion 60 thereof of various thicknesses. The resistance to fluid flow increases with an increase in the thickness of the thin portion 60.

On the upper surface of the dome 34, a radiopaque tantalum-impregnated silicone elastomer dot code 70 is situated to permit post-operative identification of the pressure/flow rating of the device 10 by X-ray photography. Furthermore, radiopaque barium seal tubes 72 and 74 are provided which wrap around a portion of the connectors 12 and 14. These radiopaque markers 70 and 72 provide means whereby a physician can detect a separation of the surgical tubing or proximal catheter from the device 10 after implantation. Such valve/tubing disconnect is readily detectable in a shunt system through the use of X-ray photography when radiopaque surgical tubing or catheters are connected to the device 10. A silicone coating 76 is applied over the dot code 70 and adjacent to ends of the seal tubes 72 and 74 to ensure proper biocompatibility of the device within the patient.

From the foregoing, it will be appreciated that the device 10 is capable of controlling the flow of cerebrospinal fluid out of a brain ventricle while preventing the backflow of fluid into the brain ventricle. The device can be fabricated conveniently and economically, is trouble-free and reliable in use, provides convenient distal flushing of the shunt system and can be easily adapted to provide a variety of pressure/flow characteristics. Further, the provision of an asymmetric membrane permits a needle to be inserted therethrough to gain proximal access to fluids upstream of the flow control member. The septum portion 58 provides a puncturable, self-sealing portion of the membrane 56, and the chance of damaging the thin portion 60 of the membrane is eliminated through the provision of a membrane shell 62 having a needle guide aperture 66 aligned over the septum portion 58 and the inlet port 42.

Although a particular embodiment of the invention has been described in detail for purposes of illustration, various modifications may be made without departing from the spirit and scope of the invention. Accordingly, the invention is not to be limited, except as by the appended claims.

We claim:

1. A surgically implantable flow control device for controlling the flow of fluid from one portion of a body to another, the device comprising:
   a base including an inlet port and a valve seat surrounding the inlet port; and
   a flow control member secured to the base and including an asymmetric membrane resiliently biased to contact the valve seat in a manner forming a releasable seal therebetween to provide controlled resistance to proximal-to-distal fluid flow through the device, the membrane including a thickened septum portion overlying the inlet port and a relatively thin portion responsive to fluid pressure differentials on inlet and outlet sides thereof.

2. The flow control device of claim 1, including an outlet separated from the inlet port by the flow control member.

3. The flow control device of claim 2, including a flexible encasement which, in connection with the base, defines a fluid reservoir between the inlet port and the outlet.

4. The flow control device of claim 3, wherein the encasement includes means for anchoring the device in place when surgically implanted.

5. The flow control device of claim 3, including a membrane shield within the fluid reservoir.

6. The flow control device of claim 5, wherein the membrane shield overlies the outlet side of the membrane and includes a needle guide aperture therethrough over the septum portion.

7. The flow control device of claim 6, wherein the needle guide aperture is aligned with the inlet port.

8. The flow control device of claim 6, including an alignment plug fixed to the septum portion and extending through the needle guide aperture.

9. The flow control device of claim 8, wherein the alignment plug comprises an elastomeric adhesive.

10. A surgically implantable flow control device for controlling the flow of fluid from one portion of a body to another, the device comprising:
    a base including an inlet port and a valve seat surrounding the inlet port;
    an inlet connector integral with the base and having a passageway therethrough terminating at the inlet port;
    a flow control member secured to the base and including a membrane resiliently biased to contact the valve seat in a manner forming a releasable seal therebetween to provide controlled resistance to proximal-to-distal fluid flow through the device, the membrane including a thickened septum portion overlying the inlet port and a relatively thin portion responsive to fluid pressure differentials on inlet and outlet sides thereof;
    an outlet separated from the inlet port by the flow control member; and
    an outlet connector integral with the base and having a passageway therethrough forming the outlet.

11. The flow control device of claim 10, including an alignment plug fixed to the membrane and extending through the needle guide aperture.

12. The flow control device of claim 11, wherein the alignment plug comprises an elastomeric adhesive.

13. The flow control device of claim 10, wherein the membrane is disposed between the inlet port and the needle guide aperture.

14. The flow control device of claim 10, wherein the membrane shield includes prongs which engage the base to hold the membrane shield in place.

15. The flow control device of claim 10, including a flexible encasement which, in connection with the base, defines a fluid reservoir between the inlet port and the outlet, wherein the encasement includes means for anchoring the device when surgically implanted.

16. A surgically implantable flow control device for controlling the flow of fluid from one portion of a body to another, the device comprising:
   a base including an inlet port and a valve seat surrounding the inlet port;
   a flow control member secured to the base and including an asymmetric membrane resiliently biased to contact the valve seat in a manner forming a releasable seal therebetween to provide controlled resistance to proximal-to-distal fluid flow through the device, the membrane including a thickened septum portion overlying the inlet port and a relatively thin portion responsive to fluid pressure differentials on inlet and outlet sides thereof; and
   means for guiding a needle inserted into the flow control device when subcutaneously implanted, through the septum portion of the membrane.

17. The flow control device of claim 16, wherein the needle guide aperture is aligned with the inlet port, and further including an alignment plug fixed to the septum portion and extending through the needle guide aperture.

18. The flow control device of claim 16, wherein the alignment plug comprises an elastomeric adhesive.

19. The flow control device of claim wherein the membrane shield includes prongs which engage the base to hold the membrane shield in place.

20. The flow control device of claim 16, including an outlet separated from the inlet port by the flow control member, an inlet connector integral with the base and have having a passageway therethrough terminating at the inlet port, and an outlet connector integral with the base and having a passageway therethrough forming the outlet.

21. The flow control device of claim 20, including a flexible encasement which, in connection with the base, defines a fluid reservoir between the inlet port and the outlet.

22. The flow control device of claim 10, including a membrane shield overlying the membrane and including a needle guide aperture therethrough in alignment with the inlet port.

23. The flow control device of claim 16, wherein the needle guiding means includes a membrane shield overlying the membrane and including a needle guide aperture therethrough over the septum portion.

* * * * *

UNITED STATES PATENT AND TRADEMARK OFFICE
CERTIFICATE OF CORRECTION

PATENT NO. : 5,800,376
DATED : September 1, 1998
INVENTOR(S) : David A. Watson and Paul S. Vaskelis It is certified that error appears in the above-identified patent and that said Letters Patent is hereby corrected as shown below:

In claim 11, line 1, delete "10" and insert --22--.

In claim 13, line 1, delete "10" and insert --22--.

In claim 14, line 1, delete "10" and insert --22--.

In claim 17, line 1, delete "16" and insert --23--.

In claim 18, line 1, delete "16" and insert --23--.

In claim 19, line 1, after "claim" insert --23,--.

Signed and Sealed this

First Day of June, 1999

Attest:

Q. TODD DICKINSON

Attesting Officer

Acting Commissioner of Patents and Trademarks

UNITED STATES PATENT AND TRADEMARK OFFICE
CERTIFICATE OF CORRECTION

PATENT NO. : 5,800,376

DATED : September 1, 1998

INVENTOR(S) : David Watson, Paul Vaskelis

It is certified that error appears in the above-identified patent and that said Letters Patent is hereby corrected as shown below:

Column 8, Line 14: "have having" should be "having"

Signed and Sealed this

Eighteenth Day of April, 2000

Attest:

Q. TODD DICKINSON

*Attesting Officer*   *Director of Patents and Trademarks*